(12) United States Patent
Miyagawa et al.

(10) Patent No.: US 10,342,594 B2
(45) Date of Patent: Jul. 9, 2019

(54) BALLOON CATHETER

(71) Applicant: Nipro Corporation, Osaka (JP)

(72) Inventors: Katsuya Miyagawa, Osaka (JP); Yuuki Nishimura, Osaka (JP); Natsumi Shimazaki, Osaka (JP)

(73) Assignee: Nipro Corporation, Osaka (JP)

(*) Notice: Subject to any disclaimer, the term of this patent is extended or adjusted under 35 U.S.C. 154(b) by 33 days.

(21) Appl. No.: 15/304,822

(22) PCT Filed: Jul. 1, 2015

(86) PCT No.: PCT/JP2015/068943
§ 371 (c)(1),
(2) Date: Nov. 15, 2016

(87) PCT Pub. No.: WO2016/013358
PCT Pub. Date: Jan. 28, 2016

(65) Prior Publication Data
US 2017/0119450 A1    May 4, 2017

(30) Foreign Application Priority Data

Jul. 24, 2014  (JP) ................. 2014-150403
Jul. 24, 2014  (JP) ................. 2014-150406

(51) Int. Cl.
*A61B 18/04*    (2006.01)
*A61B 17/00*    (2006.01)
(Continued)

(52) U.S. Cl.
CPC ............. *A61B 18/04* (2013.01); *A61B 17/00* (2013.01); *A61B 18/08* (2013.01); *A61B 18/082* (2013.01);
(Continued)

(58) Field of Classification Search
CPC ......... A61B 18/08; A61B 18/04; A61B 18/20; A61B 2018/0022; A61M 25/10
See application file for complete search history.

(56) References Cited

U.S. PATENT DOCUMENTS 4,848,339 A     7/1989  Rink et al.
4,878,492 A  *  11/1989  Sinofsky .............. A61B 18/245
                                                      606/7
(Continued)

FOREIGN PATENT DOCUMENTS

DE       4100290 A1    7/1991
EP       0448004 A2    9/1991
(Continued)

OTHER PUBLICATIONS

International Search Report issued in PCT/JP2015/068943 dated Sep. 1, 2015.
(Continued)

*Primary Examiner* — Nathan R Price
*Assistant Examiner* — Anh Bui
(74) *Attorney, Agent, or Firm* — Marshall, Gerstein & Borun LLP

(57) ABSTRACT

A balloon catheter (10) has a shaft (12) having an elastically expandable balloon (11) on the distal end side and space provided inside and allowing a fluid to flow into and flow out the balloon (11), a heat generating member (22) provided in the internal space of the balloon (11), and optical fibers (20A, 20B) which are extended up to the internal space of the balloon (11) along the shaft (12) and emit light beams input into the proximal end to the heat generating member (22) from the distal end.

4 Claims, 9 Drawing Sheets

(51) Int. Cl.
*A61F 7/12* (2006.01)
*A61B 18/20* (2006.01)
*A61M 25/10* (2013.01)
*A61B 18/08* (2006.01)
*A61B 18/00* (2006.01)

(52) U.S. Cl.
CPC ............... *A61B 18/20* (2013.01); *A61F 7/12* (2013.01); *A61M 25/10* (2013.01); *A61B 2018/0022* (2013.01); *A61B 2018/00422* (2013.01); *A61B 2018/00821* (2013.01)

(56) References Cited

U.S. PATENT DOCUMENTS

| | | |
|---|---|---|
| 4,978,346 A | 12/1990 | Bentley |
| 4,994,060 A | 2/1991 | Rink et al. |
| 5,334,206 A | 8/1994 | Daikuzono |
| 2007/0127870 A1 | 6/2007 | Oron et al. |
| 2009/0306637 A1 | 12/2009 | Esch et al. |
| 2013/0267985 A1* | 10/2013 | Arai ............... A61B 18/04 606/194 |
| 2014/0336637 A1* | 11/2014 | Agrawal ............ A61B 18/1492 606/41 |

FOREIGN PATENT DOCUMENTS

| | | |
|---|---|---|
| EP | 2653129 A1 | 10/2013 |
| JP | H01141676 A | 6/1989 |
| JP | H0392144 A | 4/1991 |
| JP | H05200045 | 8/1993 |
| JP | H05212118 A | 8/1993 |
| JP | H07213621 A | 8/1995 |
| JP | 2006015064 A * | 1/2006 |
| JP | 2006-326226 A | 12/2006 |
| JP | 2007020737 A | 2/2007 |
| JP | 2007-514117 A | 5/2007 |
| JP | 2009536546 A | 10/2009 |
| WO | WO-2012/081217 A1 | 6/2012 |

OTHER PUBLICATIONS

Supplementary European Search Report issued in European Patent Application No. 15 82 4748 dated May 23, 2018.
Partial European Search Report issued in Patent Application No. EP15824748 dated Feb. 21, 2018.

* cited by examiner

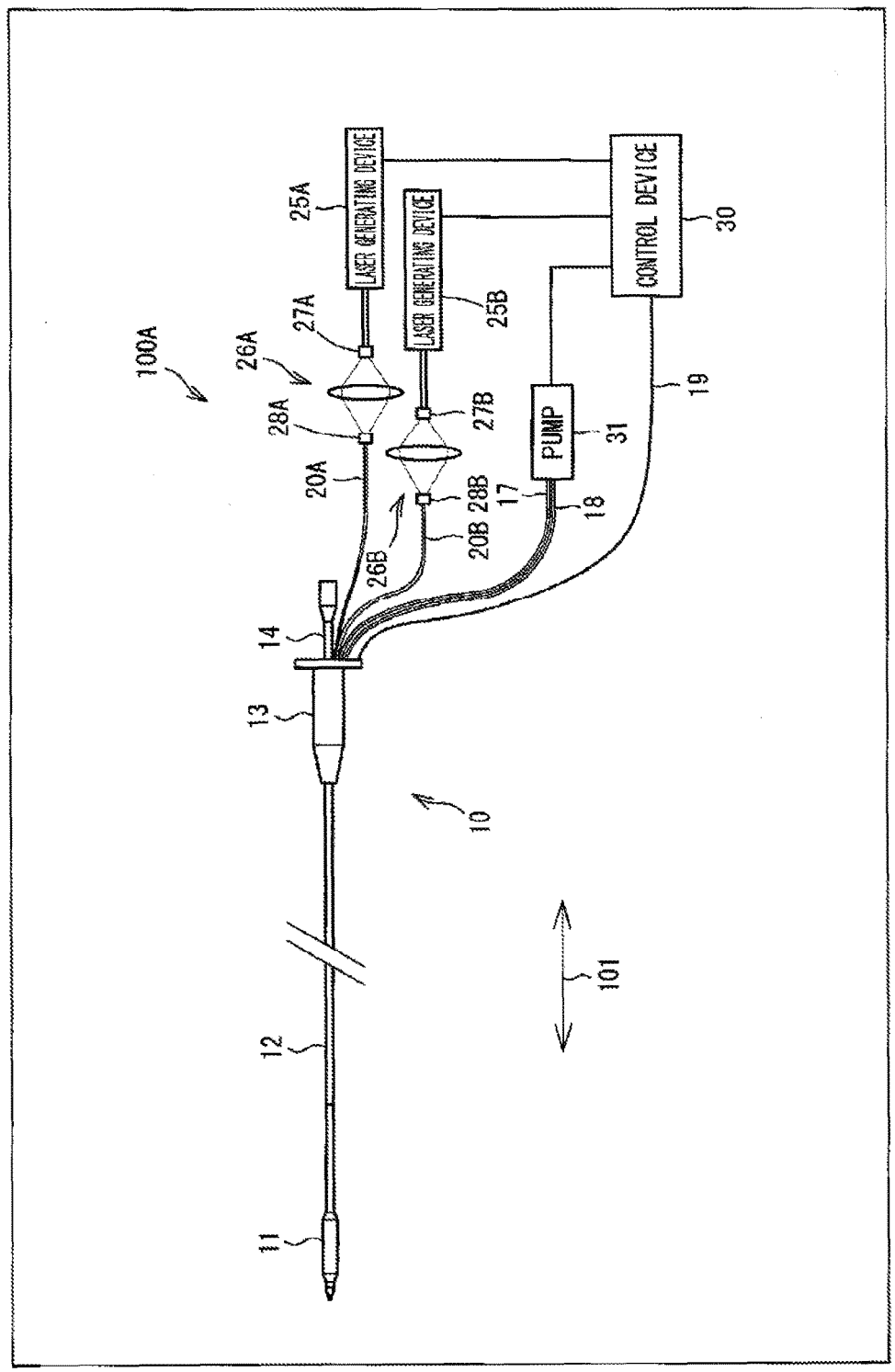
[Fig. 1]

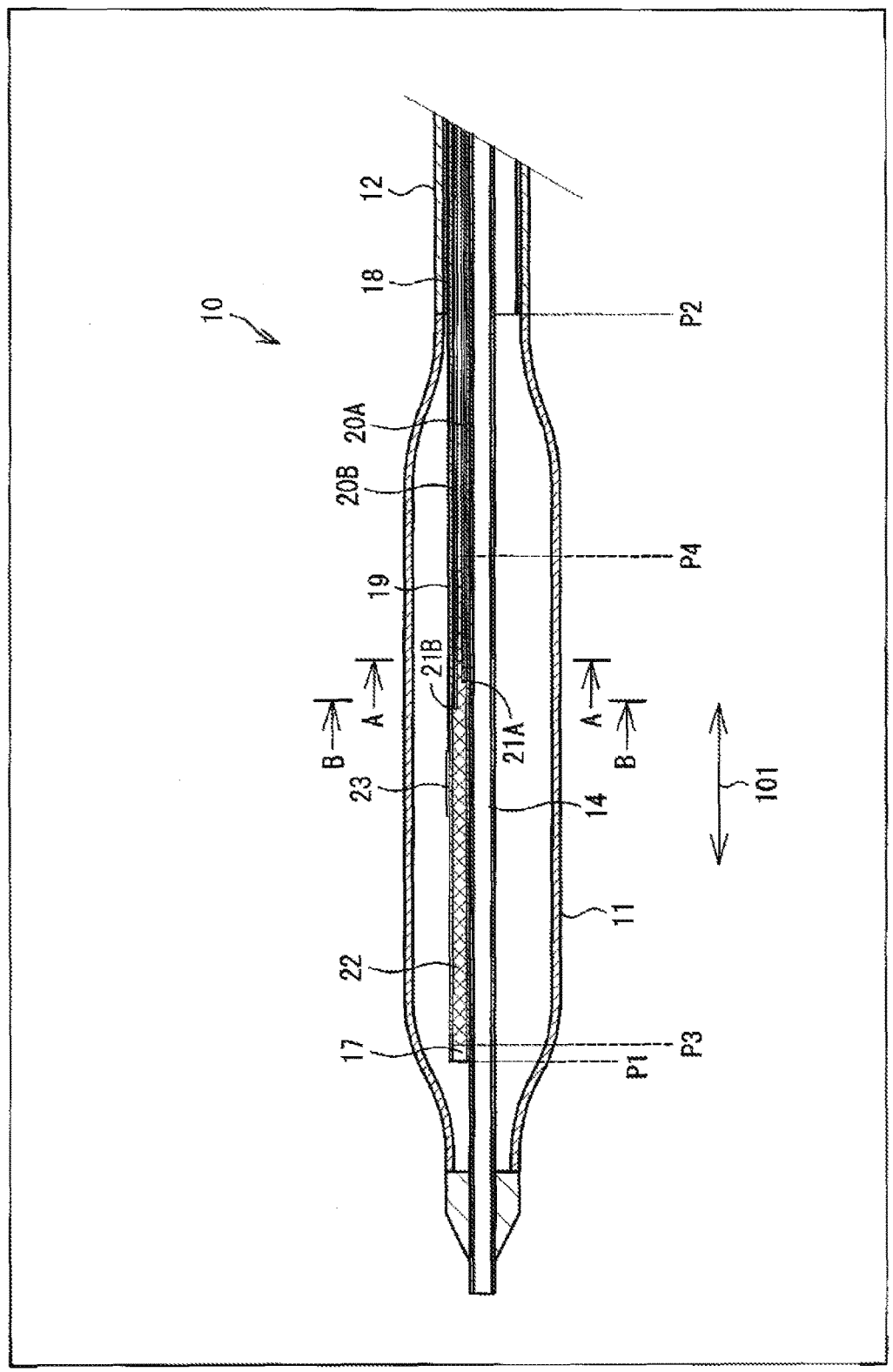
[Fig. 2]

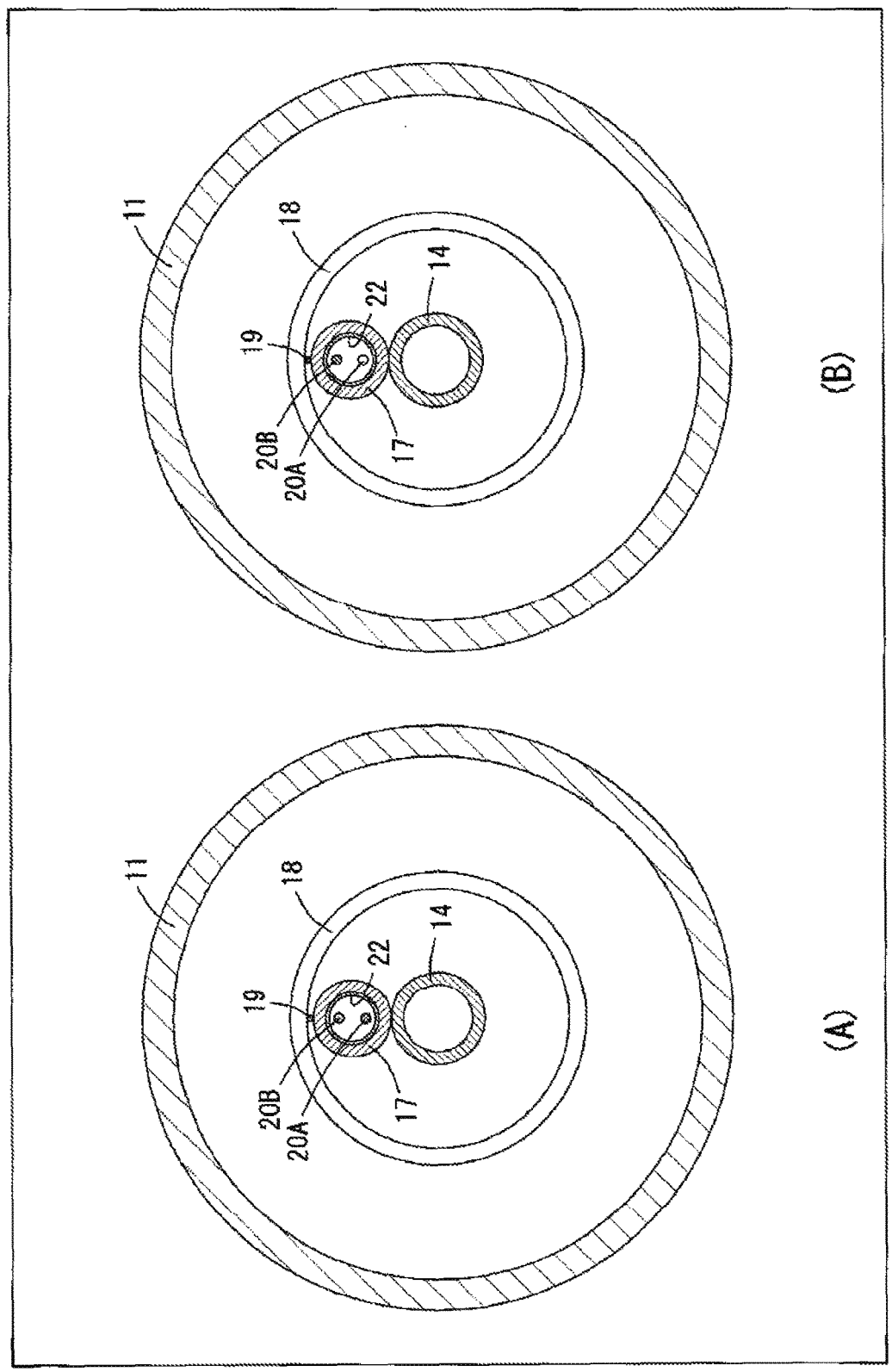
[Fig. 3]

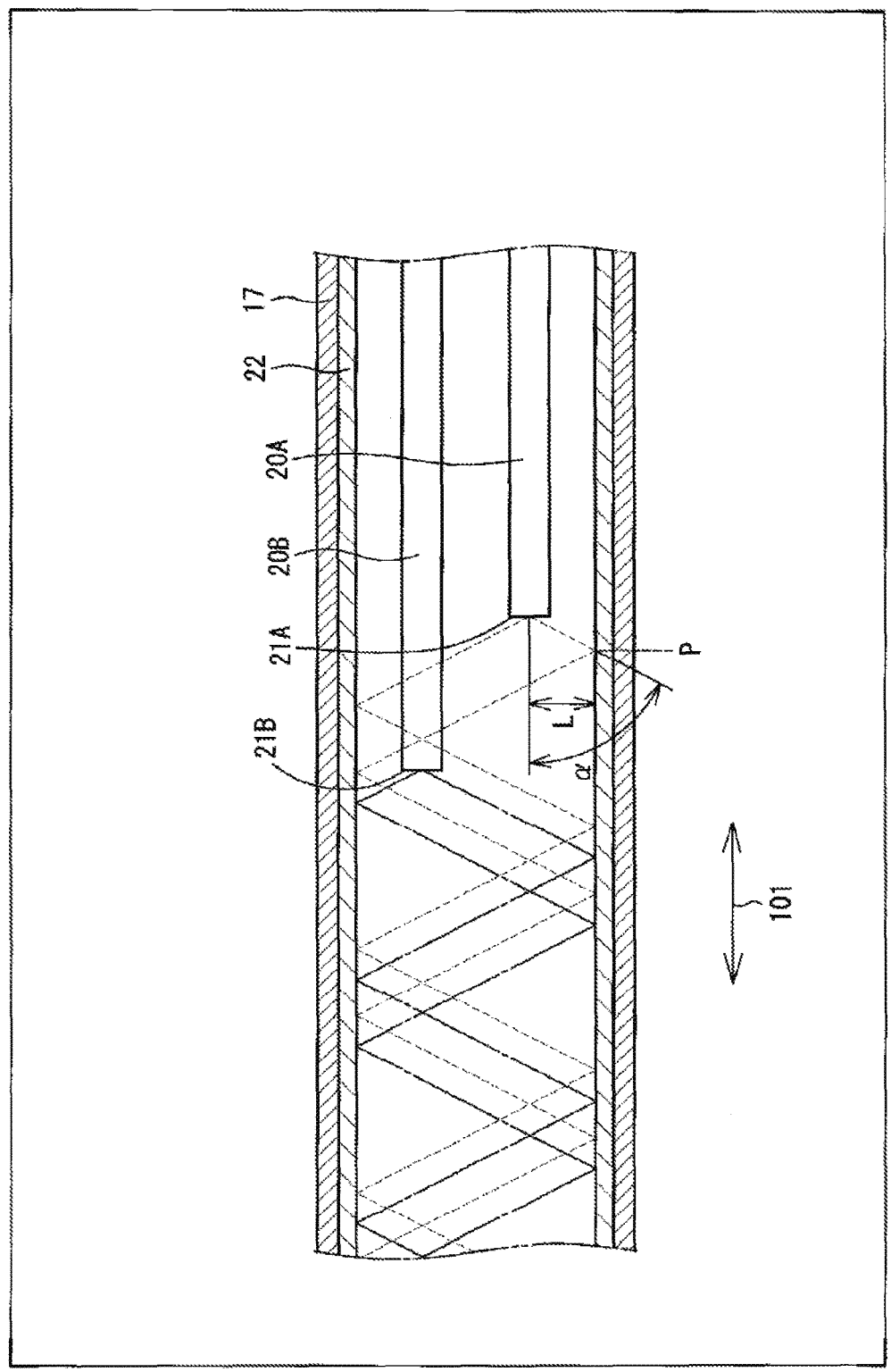
[Fig. 4]

[Fig. 5]
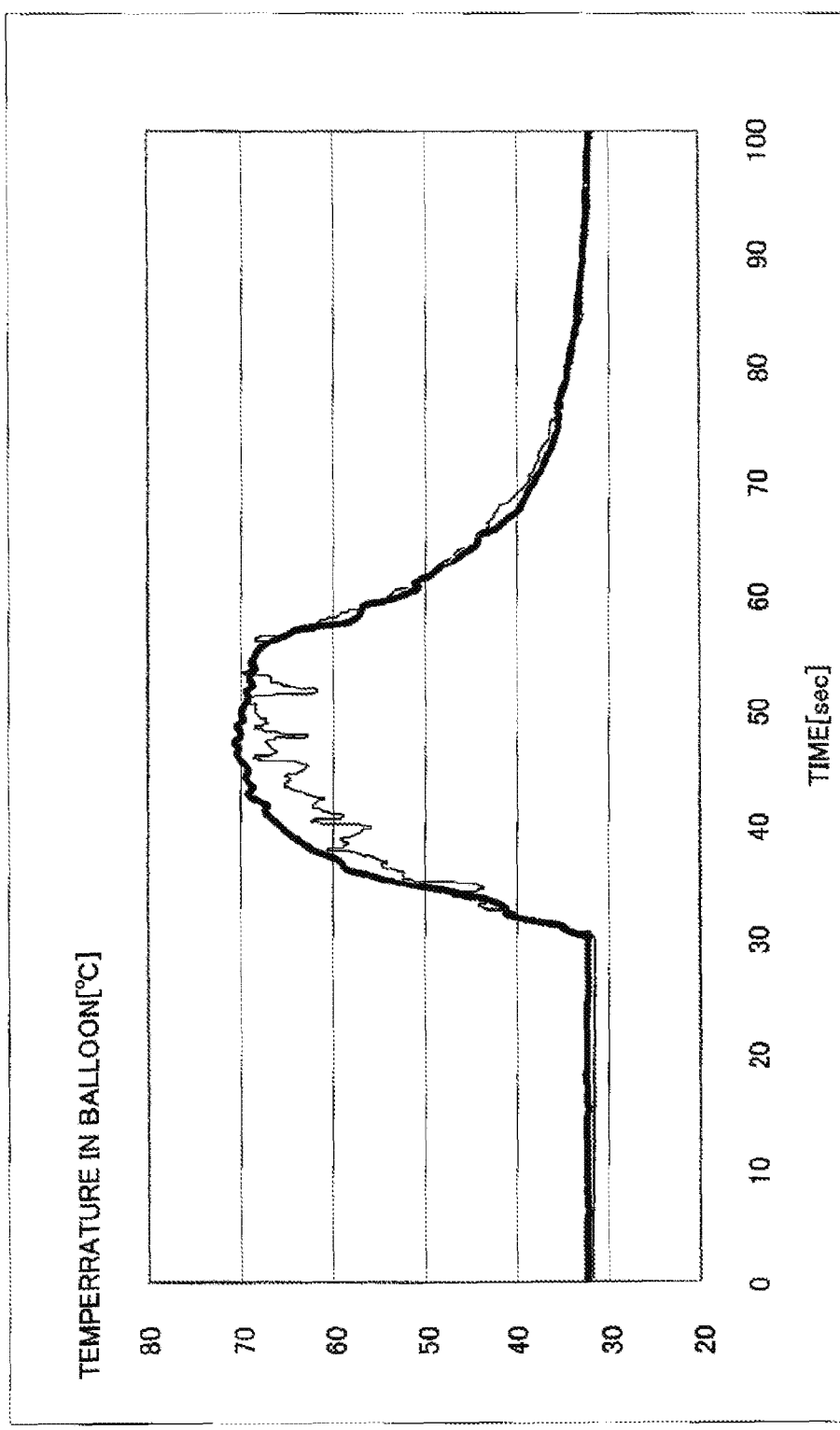

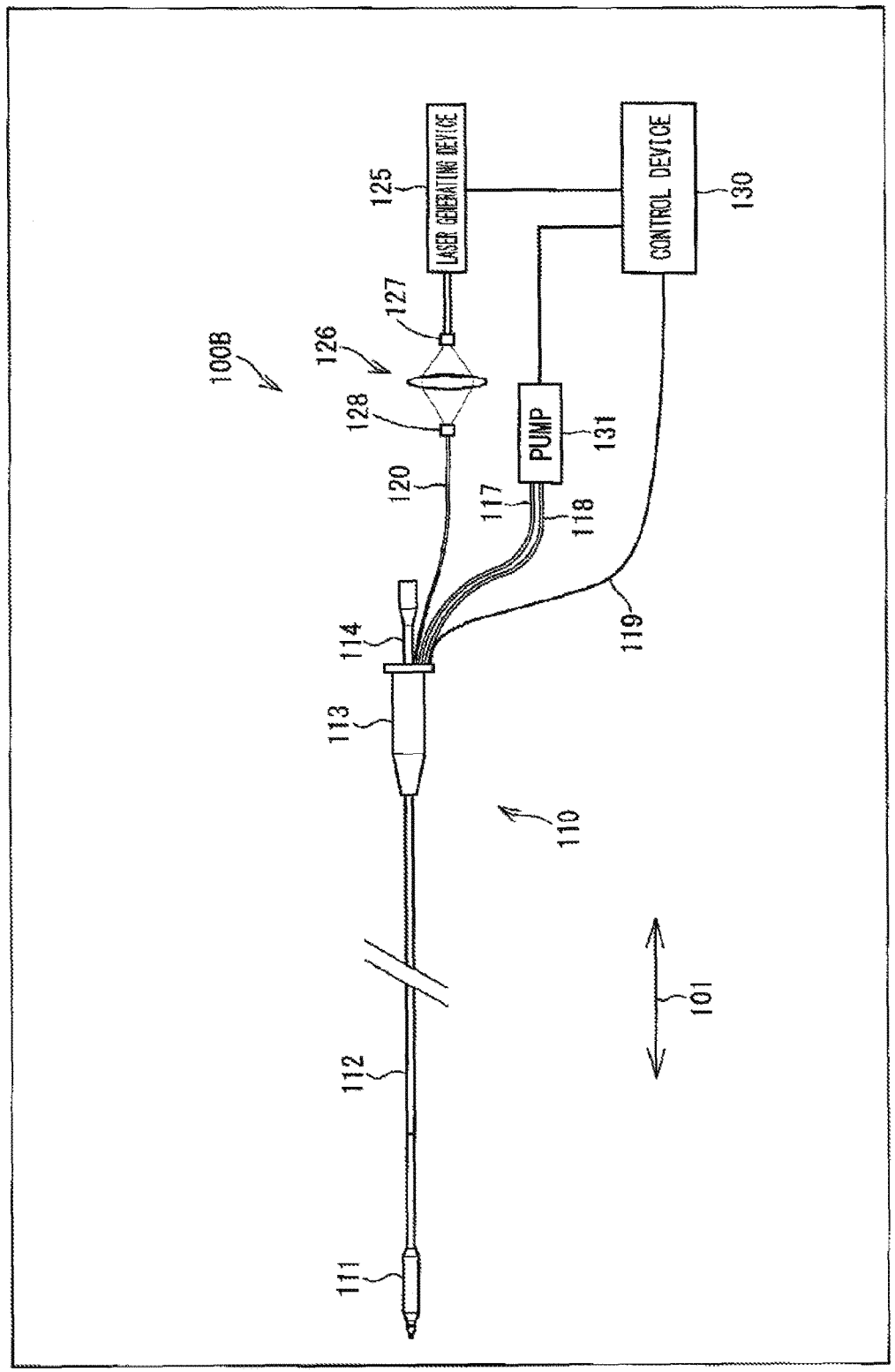
[Fig. 6]

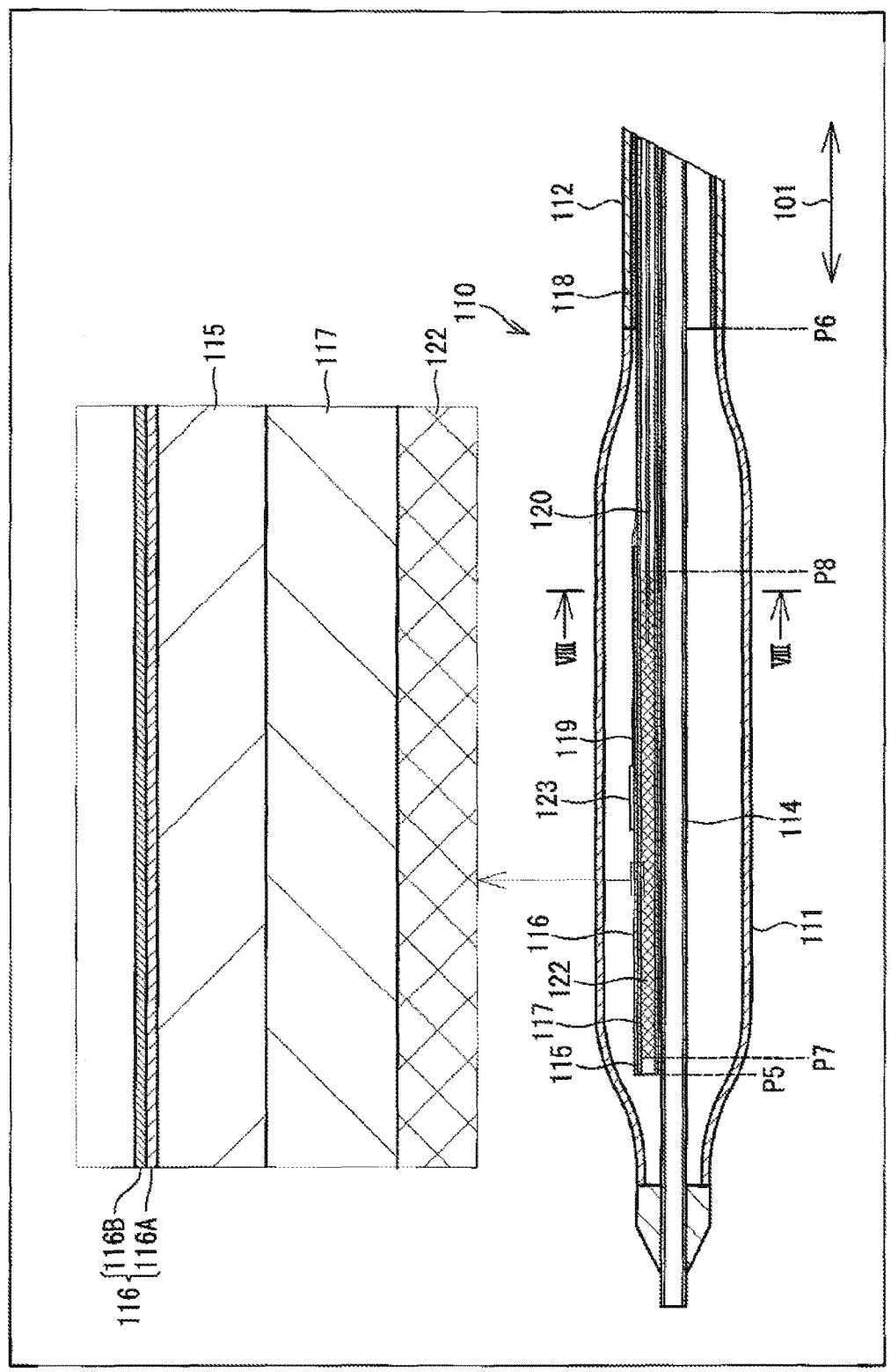
[Fig. 7]

[Fig. 8]
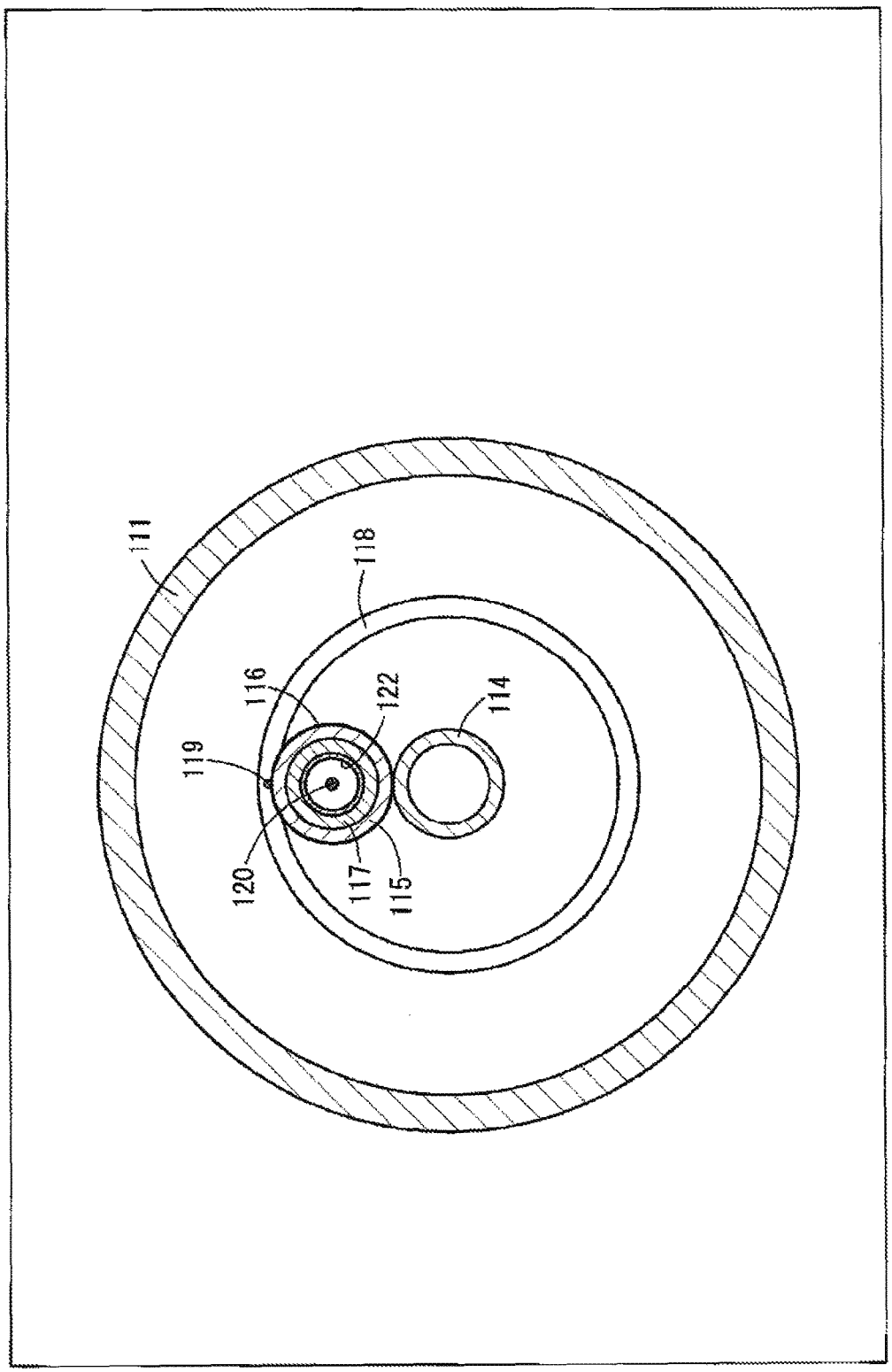

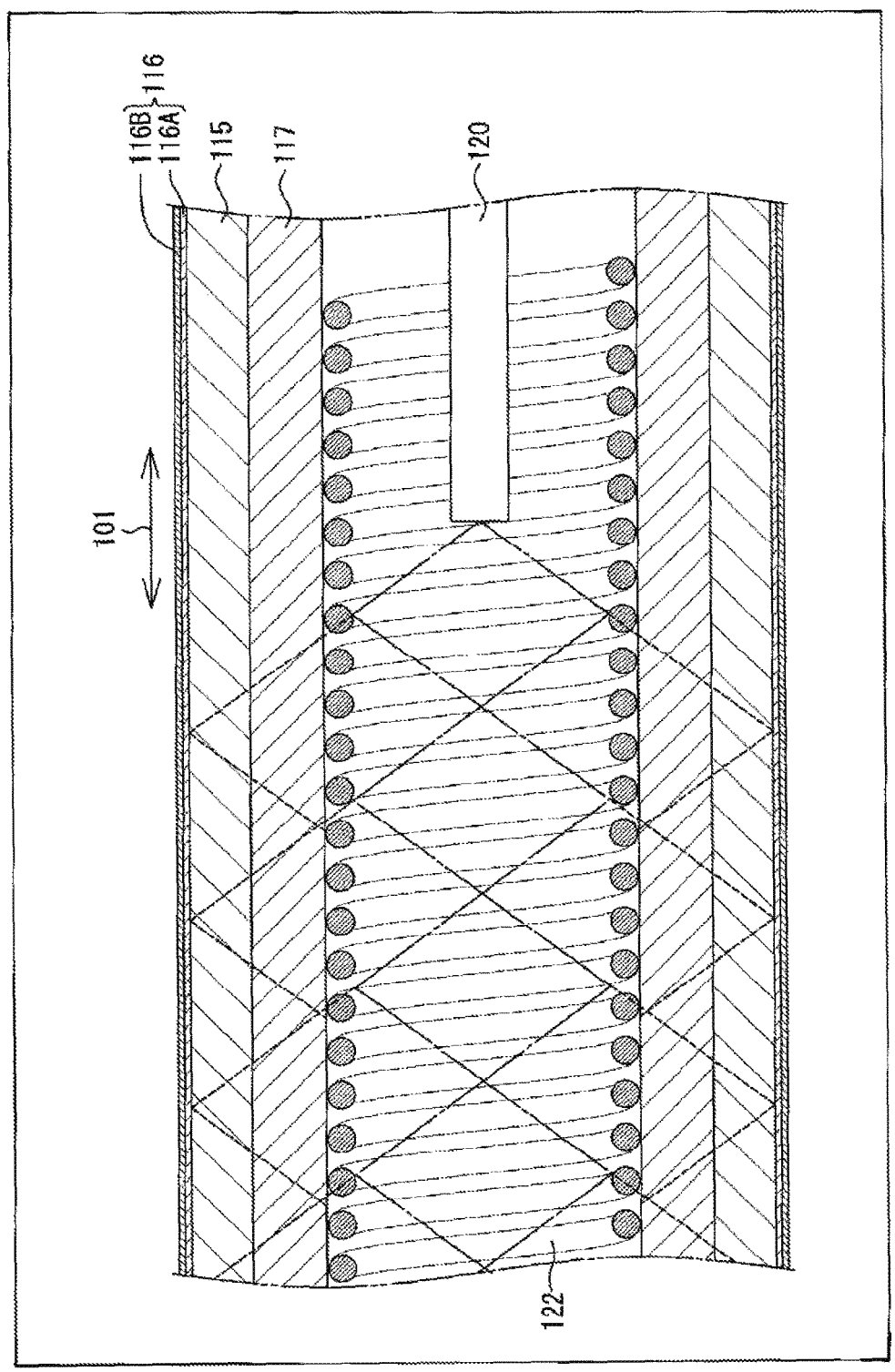
[Fig. 9]

BALLOON CATHETER

TECHNICAL FIELD

The present invention relates to a balloon catheter for use in medical treatment of expanding a stenosis portion of a blood vessel.

BACKGROUND

Heretofore, medical treatment of expanding a narrowed blood vessel by a catheter has been performed. For example, in order to expand a stenosis portion of the artery with a balloon catheter in a balloon dilation, a guide wire is inserted into a guiding catheter, so that the distal end is caused to reach the vicinity of the stenosis portion. The balloon catheter is inserted into the guiding catheter in such a manner as to be guided by the guide wire, so that a balloon portion is caused to reach the stenosis portion of the artery. Then, the balloon portion is inflated to expand the stenosis portion of the artery (refer to Patent Literatures 1 to 3).

The balloon dilation has a problem that the frequency of occurrence of restenosis after the operation is high. Although there are various opinions on the mechanism that the restenosis occurs, two phenomena mainly contribute to the occurrence of restenosis. First, the pressurization by the balloon causes mechanical damages (separation, cracking) in a vascular wall to thereby cause chronical migration and hyperproliferation of vascular cells, so that the cavity of the blood vessel is blocked. Secondly, a blood vessel itself is narrowed due to constrictive remodeling of the blood vessel. To address the problem, a technique of simultaneously performing pressurization and heating of a stenosis portion by a balloon catheter, i.e., a heating type balloon dilation, has been devised (refer to Patent Literatures 4 and 5). The heating type balloon dilation is a technique including heating a vascular wall during balloon pressurization to thereby thermally denature (soften) collagen fibers in the vascular wall to perform expansion treatment without causing separation of the vascular wall at a low expansion pressure. The technique can suppress mechanical damages of a blood vessel which is a problem of the balloon dilation.

In the above-described heating type balloon dilation, by heating a heat generating member provided in a balloon, the heat is transmitted to the vascular wall through a fluid (for example, physiological saline, water) for expanding the balloon. However, when the heating amount of the heat generating member is insufficient, the blood vessel is continuously heated over a long period of time in order to increase the temperature of the blood vessel to a target temperature. As a result, a problem that proteins forming the blood vessel are thermally denatured may arise. Moreover, this problem becomes more remarkable with an increase in the capacity of the internal space of the balloon.

Moreover, in the heating type balloon dilation, heat is transmitted to the vascular wall through a fluid (for example, physiological saline, water) for expanding a balloon from a heat generating member heated by irradiation with a light beam, for example. However, when a light source is disposed inside the heat generating member having a cylindrical shape and formed with a metal wire, a light beam emitted from the light source may leak out of a gap generated between the metal wires to the outside of the balloon catheter. This may cause a reduction in the heating efficiency of the heat generating member.

SUMMARY OF THE DESCRIPTION

The present invention has been made in view of the circumstances described above. It is an object of the present invention to provide a balloon catheter capable of increasing the temperature of a blood vessel contacting a balloon to a target temperature in a short time by efficiently heating a heat generating member in a heating type balloon dilation.

It is another object of the present invention to provide a balloon catheter of preventing a light beam emitted to a heat generating member from leaking out in a heating type balloon dilation.

(1) A balloon catheter according to the present invention has a shaft having an elastically expandable balloon on the distal end side and space provided inside and allowing a fluid to flow into and flow out of the balloon, a heat generating member provided in the internal space of the balloon, and a first light guide member and a second light guide member which are extended up to the internal space of the balloon along the shaft and emit light beams to the heat generating member from the distal end.

According to the configuration described above, the heat generating member is heated by the light beams emitted from each of the first light guide member and the second light guide member, and therefore the temperature in the balloon can be increased in a short time. As a result, the thermal denaturation of proteins by continuously heating a blood vessel over a long period of time can be suppressed.

(2) Preferably, the positions of the distal ends of the first light guide member and the second light guide member are shifted from each other in the extending direction.

According to the configuration described above, positions where the light beam emitted from each of the first light guide member and the second light guide member reaches the heat generating member first can be shifted from each other. Thus, the temperature of the heat generating member can be uniformly increased and damages of the heat generating member due to overheating can be suppressed.

(3) Preferably, the first light guide member and the second light guide member are fixed to each other.

According to the configuration described above, even when the balloon catheter is curved in a blood vessel, a fluctuation of the shift amount of the positions of the distal ends of the first light guide member and the second light guide member can be suppressed.

(4) For example, the first light guide member and the second light guide member emit diffused light beams inside the heat generating member having a cylindrical shape. The position of the distal end of the second light guide member in the extending direction is located on the distal end side of the heat generating member relative to the position where the light beam emitted from the first light guide member reaches the heat generating member first.

(5) For example, the heat generating member is obtained by winding a metal wire in a coil shape.

(6) A balloon catheter in the present invention has a tubular shaft having an elastically expandable balloon on the distal end side, a tube which is inserted into the shaft to be extended up to the internal space of the balloon and allows a fluid to flow into the balloon, a heat generating member which is of a cylindrical shape, is formed with a metal wire, and is extended along the inner wall surface of the tube in the internal space of the balloon, a light guide member which is inserted into the tube to be extended up to the inside of the heat generating member and which emits light beams input into the proximal end to the heat generating member from the distal end, and a cover tube which covers the tube at a position where the cover tube is superimposed on the heat generating member in the radial direction and which has a light-reflective metal layer laminated on at least one of the inner wall surface and the outer wall surface.

According to the above-described configuration, even when the light beams emitted from the light guide member partially pass through the heat generating member, the light beams are reflected on a metal layer, so that the light beams are prevented from leaking out to the outside of the balloon catheter. Moreover, since the light beams reflected on the metal layer are emitted to the heat generating member again, the heat generating member can be efficiently heated.

(7) For example, the metal layer contains a first metal layer formed on the wall surface of the cover tube by electroless plating and a second metal layer formed on the surface of the first metal layer by electrolytic plating.

(8) Preferably, a material forming the first metal layer is nickel or copper.

Nickel is more preferable than copper in the respect that the adhesiveness with the cover tube is high. On the other hand, from the viewpoint of preventing breakage of the first metal layer due to overheating when the outputs of the light beams emitted from the light guide member are high or the quantity of the light beams passing through the heat generating member is large, for example, copper having light absorptivity and thermal conductivity higher than those of nickel is preferably employed.

(9) Preferably, a material forming the second metal layer is silver, gold, or platinum.

By forming the second metal layer with a material having high biocompatibility as in the above-described configuration, even when the balloon is broken in the blood vessel, influence on a living body can be minimized.

(10) For example, the tube is formed with a thermoplastic elastomer having flexibility. The cover tube is formed with polyimide.

According to the present invention, the heat generating member is efficiently heated by the light beams emitted from each of the first light guide member and the second light guide member, and therefore the temperature of a blood vessel contacting the balloon can be increased to a target temperature in a short time.

Moreover, the present invention can provide a balloon catheter in which a light beam is prevented from leaking out to the outside by causing the metal layer to reflect the light beam passing through the heat generating member.

BRIEF DESCRIPTION OF DRAWINGS

FIG. 1 is a view illustrating the external configuration of a balloon catheter device 100A in a state where a balloon 11 is in a contracted attitude.

FIG. 2 is a cross sectional view of the balloon 11.

FIG. 3(A) is a cross sectional view along the A-A line of FIG. 2

FIG. 3(B) is a cross sectional view along the B-B line of FIG. 2.

FIG. 4 is a view illustrating the paths of laser light beams emitted from optical fibers 20A and 20B.

FIG. 5 is a view showing temperature changes (thick line) in the balloon 11 when a heat generating member 22 is heated by the optical fibers 20A and 20B in which the positions of distal ends are shifted from each other and temperature changes (thin line) in the balloon 11 when the heat generating member 22 is heated by the optical fibers 20A and 20B in which the positions of distal ends are in agreement with each other.

FIG. 6 is a view illustrating the external configuration of a balloon catheter device 100B in a state where a balloon 111 is in a contracted attitude.

FIG. 7 is a cross sectional view of the balloon 111.

FIG. 8 is a cross sectional view along the VIII-VIII line of FIG. 7.

FIG. 9 is a view illustrating the paths of laser light beams emitted from an optical fiber 120.

DETAILED DESCRIPTION

Hereinafter, preferable embodiments of the present invention are described with reference to the drawings. Embodiments 1 and 2 describe only one embodiment of the present invention. It is a matter of course that the embodiments can be altered insofar as the scope of the present invention is not altered. The embodiments 1 and 2 can be combined.

[Embodiment 1]

A balloon catheter device 100A in an embodiment 1 has a balloon catheter 10, a plurality of laser generating devices 25A and 25B, a plurality of light converging optical system units 26A and 26B, a control device 30, and a pump 31 as illustrated in FIG. 1. In the embodiment 1, the laser generating devices 25A and 25B and the light converging optical system units 26A and 26B of the balloon catheter device 100A have two systems but may have three or more systems.

The balloon catheter 10 has a shaft 12 having a balloon 11 on the distal end side as illustrated in FIG. 1 and FIG. 2. The shaft 12 is a member long in an axial direction 101. The shaft 12 is a tubular body which can be elastically bent in such a manner as to be curved with respect to the axial direction 101. A direction where the shaft 12 in a state where the shaft 12 is not curved is extended is defined as the axial direction 101 in this specification. In the balloon catheter 10 illustrated in FIG. 1, the backside (right side in FIG. 1) with respect to a direction in which the balloon catheter 10 is inserted into a blood vessel is defined as a "proximal end side" and a front side (left side in FIG. 1) with respect to the direction in which the balloon catheter 10 is inserted into a blood vessel is defined as a "distal end side".

As illustrated in FIG. 2, a guide wire tube 14, an in-side tube 17, an out-side tube 18, a cable 19, and optical fibers 20A and 20B are inserted into and passed through the shaft 12. The outer diameter and the inner diameter of the shaft 12 do not necessarily need to be fixed with respect to the axial direction 101. However, from the viewpoint of operability, it is preferable that the rigidity of the proximal end side is higher than the rigidity of the distal end side. For the shaft 12, known materials for use in balloon catheters, such as synthetic resin and stainless steel, can be used. The shaft 12 does not necessarily need to contain only one kind of raw material and may be formed by attaching a plurality of parts containing different raw materials.

The balloon 11 provided on the distal end side of the shaft 12 is elastically expanded when a fluid (liquid, gas) flows into the internal space through the in-side tube 17 and is contracted when the liquid flows out of the internal space through the out-side tube 18. More specifically, the internal space of the balloon 11 communicates with the internal space of each of the in-side tube 17 and the out-side tube 18 inserted into and passed through the shaft 12. With respect to the size of the balloon 11, the length in the axial direction 101 is about 20 mm to 40 mm and the diameter when expanded is about 6 mm to 8 mm, for example. FIG. 1 and FIG. 2 illustrate the balloon 11 in the contracted state. For materials of the balloon 11 and a method for fixing the balloon 11 and the shaft 12, known raw materials and known methods for use in balloon catheters can be used.

On the distal end side of the shaft 12, a hub 13 is provided. The guide wire tube 14, the in-side tube 17, the out-side tube 18, the cable 19, and the optical fibers 20A and 20B are inserted into and passed through the shaft 12 through the hub 13 and are extended in the axial direction 101. More specifically, the extending directions of the guide wire tube 14, the in-side tube 17, the out-side tube 18, the cable 19, and the optical fibers 20A and 20B in the shaft 12 are substantially in agreement with the axial direction 101. The guide wire tube 14 and the in-side tube 17 are adjacent to each other inside the out-side tube 18 as illustrated in FIG. 3(A) and FIG. 3(B). The optical fibers 20A and 20B are adjacent to each other inside the in-side tube 17 as illustrated in FIG. 3(A). Materials forming the guide wire tube 14, the in-side tube 17, and the out-side tube 18 are not particularly limited and can be formed with a thermoplastic elastomer having flexibility, such as Pebax (Registered Trademark), for example.

As illustrated in FIG. 1 and FIG. 2, the distal end of the guide wire tube 14 inserted into and passed through the inside of the shaft 12 through the hub 13 is exposed to the outside from the distal end side of the balloon 11 and is opened. The guide wire tube 14 in the balloon 11 is provided with a marker containing a contrast medium as the raw material. Examples of the contrast medium include barium sulfate, bismuth oxide, and bismuth subcarbonate, for example.

As illustrated in FIG. 2, the position of the distal end of the in-side tube 17 inserted into and passed through the inside of the shaft 12 through the hub 13 is a position P1 and the position of the distal end of the out-side tube 18 inserted into and passed through the inside of the shaft 12 through the hub 13 is a position P2. More specifically, the distal end of the in-side tube 17 is located on the distal end side of the balloon 11 relative to the distal end of the out-side tube 18. In other words, the distal end side of the in-side tube 17 is partially exposed from the out-side tube 18. However, the positional relationship between the distal ends of the in-side tube 17 and the out-side tube 18 is not limited thereto.

End portions on the proximal end side of the in-side tube 17 and the out-side tube 18 are connected to a pump 31 as illustrated in FIG. 1. When the pump 31 is driven, a fluid flows into the internal space of the balloon 11 through the in-side tube 17 and a fluid flowing out of the balloon 11 returns to the pump 31 through the out-side tube 18. Then, due to the fact that a fluid continuously flows into the balloon 11 at pressure required for the balloon 11 to maintain expansion, the balloon 11 expands in the radial direction orthogonal to the axial direction 101, so that the diameter of the center in the axial direction 101 reaches the maximum diameter. The internal space of the in-side tube 17 is equivalent to the space for allowing a fluid to flow into the balloon 11. The internal space of the out-side tube 18 is equivalent to the space for allowing a fluid to flow out of the balloon 11.

As illustrated in FIG. 2 to FIG. 4, a heat generating member 22 is provided inside the in-side tube 17 on the distal end side. In the embodiment 1, the position of the distal end of the heat generating member 22 is a position P3 and the position of the proximal end of the heat generating member 22 is a position P4. More specifically, the heat generating member 22 is provided along the inner wall surface of a portion exposed from the out-side tube 18 of the in-side tubes 17. The length in the axial direction 101 of the heat generating member 22 is about 17 mm to 35 mm and is selected as appropriate according to the length in the axial direction 101 of the balloon 11, for example.

The heat generating member 22 is a cylindrical member covering the inner wall surface of the in-side tube 17 and is obtained by winding a metal wire in a coil shape, for example. However, a specific configuration of the heat generating member 22 is not limited thereto and may be a configuration in which a metal wire is knitted in a lattice shape, a film or dot-like deposits sputtered onto the inner wall surface of the in-side tube 17, or the like, for example. Thus, the heat generating member 22 can be curved along the shape of a blood vessel into which the balloon catheter 10 is inserted. The heat generating member 22 is formed with stainless steel, for example.

As illustrated in FIG. 2, a temperature sensor 23 is provided in the internal space of the balloon 11. The installation position of the temperature sensor 23 is not particularly limited insofar as the temperature sensor 23 is installed at a position where the temperature sensor 23 contacts a fluid flowing out of the in-side tube 17. In the embodiment 1, the temperature sensor 23 is installed on the outer wall surface of a portion exposed from the out-side tube 18 of the in-side tubes 17. A specific example of the temperature sensor 23 is not particularly limited and known substances, such as a thermocouple, can be used, for example. The cable 19 is extended in the axial direction 101 along the outer wall surface of the in-side tube 17 and electrically connects the temperature sensor 23 and the control device 30. More specifically, an output signal from the temperature sensor 23 is transmitted to the control device 30 through the cable 19.

The laser generating devices 25A and 25B are known devices outputting a laser light beam generated under control by the control device 30. The wavelengths and the outputs of laser light beams to be generated are not particularly limited. The laser generating devices 25A and 25B in the embodiment 1 can output a near-infrared laser light beam of 25 W at the maximum. The light converging optical system units 26A and 26B have optical elements, such as a condensing lens, and connectors 27A, 27B, 28A, and 28B provided at both ends of optical paths of light beams passing through the optical elements. The connectors 27A and 27B are connected to the laser generating devices 25A and 25B, respectively, and the connectors 28A and 28B are connected to the optical fibers 20A and 20B, respectively. These light converging optical system units 26A and 26B diffuse once laser light beams input from the laser generating devices 25A and 25B through the connectors 27A and 27B, respectively, and condense the laser light beams again, and then output the laser light beams to the optical fibers 20A and 20B through the connectors 28A and 28B, respectively.

The optical fibers 20A and 20B inserted into and passed through the inside of the shaft 12 through the hub 13 are inserted into the internal space of the in-side tube 17 in the middle of the shaft 12. Then, the optical fibers 20A and 20B are extended up to the inside of the heat generating member 22 along the shaft 12. The optical fibers 20A and 20B are inserted into and passed through the in-side tube 17 in a state where the optical fibers 20A and 20B are fixed to each other. A specific method for fixing the optical fibers 20A and 20B is not particularly limited. The optical fibers 20A and 20B can be bonded to each other with an ultraviolet curable adhesive, for example. The optical fiber 20A is equivalent to the first light guide member and the optical fiber 20B is equivalent to the second light guide member.

The optical fibers 20A and 20B emit laser light beams input into the proximal end side through the light converging optical system units 26A and 26B to the heat generating member 22 from distal ends 21A and 21B, respectively. Specifically, laser light beams generated by the laser generating devices 25A and 25B are input into the proximal ends of the optical fibers 20A and 20B through the light converging optical system units 26A and 26B, respectively, transmitted to the distal end side while repeating total reflection in the optical fibers 20A and 20B, and then emitted to the heat generating member 22 as diffused light beams from the distal ends 21A and 21B.

The laser light beams output from the distal ends 21A and 21B of the optical fibers 20A and 20B, respectively, travel to the distal end side while repeating reflection on the inner wall surface of the heat generating member 22 as illustrated in FIG. 4. The laser light beams emitted from the optical fibers 20A and 20B heat the heat generating member 22. In FIG. 4, the paths of laser light beams having the largest diffusion angle emitted from the optical fiber 20A are indicated by the dashed lines and the paths of laser light beams having the largest diffusion angle emitted from the optical fiber 20B are indicated by the alternate long and short dash lines. The maximum diffusion angle of the laser light beams fluctuates depending on the diameters of the optical fibers 20A and 20B, the frequencies of the laser light beams, and the like.

The distal ends 21A and 21B of the optical fibers 20A and 20B, respectively, in the axial direction 101 are located inside the heat generating member 22 as illustrated in FIG. 2. More specifically, the distal ends 21A and 21B are located on the proximal end side relative to the center of the heat generating member 22 in the axial direction 101. The distal ends 21A and 21B of the optical fibers 20A and 20B, respectively, are shifted from each other in the axial direction 101. In the embodiment 1, the distal end 21B of the optical fiber 20B is located on the distal end side of the heat generating member 22 relative to the distal end 21A of the optical fiber 20A. The shift amount of the distal ends 21A and 21B in the axial direction 101 fluctuates depending on the distance between the optical fibers 20A and 20B and the heat generating member 22, the diffusion angle of laser light beams, and the like.

For example, the distal end 21B of the optical fiber 20B is preferably located on the distal end side of the heat generating member 22 relative to the position P where the laser light beam emitted from the optical fiber 20A reaches the heat generating member 22 first as illustrated in FIG. 4. The position P can be specified using a trigonometric function in which the diffusion angle (angle formed by the laser light beam with respect to the axial direction 101) of the laser light beam illustrated by the dashed line is defined as a and the distance between the output position of the laser light beam of the optical fiber 20A and the heat generating member 22 is defined as L. The shift amount of the distal ends 21A and 21B in this case is set to about 3 mm to 7 mm and is preferably set to about 5 mm, for example. The optical fibers 20A and 20B are inserted into the in-side tube 17 while being fixed to each other in a state where the distal ends 21A and 21B are shifted from each other.

The control device 30 has an arithmetic unit controlling the entire balloon catheter device 100A. Specifically, the control device 30 measures the temperature in the balloon 11 based on an output signal obtained from the temperature sensor 23 through the cable 19. The control device 30 causes the laser generating devices 25A and 25B to output laser light beams of predetermined outputs. The outputs and the irradiation time of the laser light beams are controlled based on the temperature in the balloon 11 specified by an output signal from the temperature sensor 23, for example. Furthermore, the control device 30 causes the pump 31 connected to the in-side tube 17 and the out-side tube 18 to output a fluid of a predetermined pressure and a predetermined flow rate. The fluid output from the pump 31 flows into the internal space of the balloon 11 through the in-side tube 17 and returns to the pump 31 through the out-side tube 18.

[Directions for Use of Balloon Catheter Device 100A]

Hereinafter, the directions for use of the balloon catheter device 100A are described.

The balloon catheter 10 is inserted into a blood vessel in order to expand a stenosis portion. A guide wire (not-illustrated) inserted into and passed through the blood vessel beforehand reaches the stenosis portion. The insertion of such a guide wire is performed by known techniques described in Japanese Patent Laid-Open Nos. 2006-326226 and 2006-230442, for example.

When the balloon catheter 10 is inserted into the blood vessel, a fluid is not pressed into the balloon 11, so that the balloon 11 is in a contracted state. The balloon catheter 10 in this state is inserted into a blood vessel along the guide wire inserted from the opening at the distal end of the guide wire tube 14. The insertion position of the balloon catheter 10 in the blood vessel is grasped by, for example, confirming a marker installed on the guide wire tube 14 by radiation.

After the balloon 11 reaches a desired position in the blood vessel, the pump 31 is driven under control by the control device 30, whereby a fluid flows into the in-side tube 17. The laser generating devices 25A and 25B generate laser light beams under control by the control device 30. The laser light beams emitted from the optical fibers 20A and 20B reach the heat generating member 22. A part of the laser light beams are absorbed to increase the temperature of the heat generating member 22. The other part of the laser light beams are reflected on the heat generating member 22, and travel to the distal end side of the heat generating member 22. More specifically, the laser light beams are gradually attenuated in the process of travelling to the distal end side of the heat generating member 22. The fluid flowing through the inside of the in-side tube 17 is heated by the heat generating member 22, flows into the internal space of the balloon 11, and then flows out of the balloon 11 through the out-side tube 18. The fluid flowing into the internal space of the balloon 11 expands the balloon 11 and heats the balloon 11. Thus, the pressurization due to the expansion of the balloon 11 and the heating by the generation of heat by the heat generating member 22 can be made to act on the stenosis portion of the blood vessel.

In the heating type balloon dilation in the embodiment 1, in order to increase the temperature at a position having a depth from the cavity of the blood vessel of 0.7 mm to 55° C. (target temperature), it is necessary to increase the temperature of the balloon 11 to 70±5° C. The heating time (elapsed time after the temperature in the balloon 11 reaches a predetermined temperature) is about 17.0 seconds when the temperature in the balloon 11 is set to 65° C., is about 5.6 seconds when the temperature in the balloon 11 is set to 70° C., and is about 2.8 seconds when the temperature in the balloon 11 is set to 75° C., for example. The outputs and the irradiation time of the laser light beams are controlled by the control device 30 based on a model function showing temperature changes of the balloon 11 to the irradiation time of the laser light beam, an output signal from the temperature sensor 23, and the like.

[Operational Effects of Embodiment 1]

According to the embodiment 1, the heat generating member 22 is heated by the laser light beams emitted from each of the optical fibers 20A and 20B. Thus, the temperature in the balloon 11 can be increased in a shorter time than in a case of using one optical fiber. As a result, the thermal denaturation of proteins due to continuous heating of the blood vessel over a long period of time can be suppressed.

In FIG. 5, the temperature changes with time in the balloon 11 when the heat generating member 22 is heated by the optical fibers 20A and 20B in which the positions of the distal ends are 5 mm shifted is shown by the thick line and the temperature changes with time in the balloon 11 when the heat generating member 22 is heated by the optical fibers 20A and 20B in which the positions of the distal ends are in agreement with each other is shown by the thin line. In an experiment of FIG. 5, the laser generating devices 25A and 25B are caused to generate laser beams for 25 seconds in a state where the flow rate of the fluid supplied through the in-side tube 17 is set to 0.20 mL/s and the balloon 11 inserted into a silicon tube having an inner diameter of 7 mm and a thickness of 1 mm is immersed in a 37° C. thermostat.

As is clear from FIG. 5, by shifting the positions of the distal ends of the optical fibers 20A and 20B, the time until the temperature in the balloon 11 reaches 70° C. is shortened and the temperature changes during irradiation with laser light beams (period from 30 seconds to 55 seconds of FIG. 5) are smoothened as compared with the case where the positions of the distal ends of the optical fibers 20A and 20B are in agreement with each other. As a result, the temperature of the heat generating member 22 can be uniformly increased and damages of the heat generating member 22 due to overheating can be suppressed.

Furthermore, according to the embodiment 1, the optical fibers 20A and 20B are inserted into and passed through the shaft 12 in the state where the distal ends 21A and 21B are shifted from each other and the optical fibers 20A and 20B are fixed to each other. Thus, even when the balloon catheter 10 is curved in a blood vessel, the fluctuation of the shift amount of the positions of the distal ends of the optical fibers 20A and 20B can be effectively suppressed.

When the distal ends 21A and 21B of the optical fibers 20A and 20B are disposed at positions close to the distal end of the heat generating member 22, most of the emitted laser light beams pass through the heat generating member 22 without being converted to heat. Thus, the distal ends 21A and 21B of the optical fibers 20A and 20B, respectively, are preferably disposed on the proximal end side (i.e., proximal end side relative to a central portion of the heat generating member 22 in the axial direction 101) of the heat generating member 22 in a state of being shifted by about 3 mm to 7 mm (preferably 5 mm) in the axial direction 101.

Although the embodiment 1 describes the example in which the heat generating member 22 is disposed along the inner wall surface of the in-side tube 17 and the optical fibers 20A and 20B are inserted into and passed through the in-side tube 17, the present invention is not limited thereto. More specifically, the heat generating member 22 may be disposed at a position where heat can be transmitted to a fluid flowing into the balloon 11. The optical fibers 20A and 20B may be disposed at positions where the optical fibers 20A and 20B can irradiate the heat generating member 22 with laser light beams.

Although the embodiment 1 describes the example of the balloon catheter 10 having the two optical fibers 20A and 20B, the balloon catheter of the present invention is not limited thereto and may have three or more optical fibers. In this case, the number of the laser generating devices and the light converging optical systems to be disposed is the same as the number of the optical fibers. The light beams to be transmitted through the optical fibers 20A and 20B are not limited to laser light beams having high directivity and may be diffused light beams.

Furthermore, the embodiment 1 describes the example in which a fluid is caused to flow into the balloon 11 through the in-side tube 17 and a fluid is caused to flow out of the balloon 11 through the out-side tube 18 (i.e., fluid is caused to return). However, the present invention is not limited thereto and may be configured so that a fluid is caused to flow into the balloon 11 through the in-side tube 17 and a fluid is caused to flow out of the balloon 11 through the in-side tube 17 after the completion of the balloon dilation.

[Embodiment 2]

A balloon catheter device 100B according to an embodiment 2 has a balloon catheter 110, a laser generating device 125, a light converging optical system unit 126, a control device 130, and a pump 131 as illustrated in FIG. 6. In the embodiment 2, the laser generating device 125 and the light converging optical system unit 126 of the balloon catheter device 100B have one system but may have two or more systems.

The balloon catheter 110 has a shaft 112 having a balloon 111 on the distal end side as illustrated in FIG. 6 and FIG. 7. The shaft 112 is a member long in the axial direction 101. The shaft 112 is a tubular body which can be elastically bent in such a manner as to be curved with respect to the axial direction 101. A direction where the shaft 112 in a state where the shaft 112 is not curved is extended is defined as the axial direction 101 in this specification. In the balloon catheter 110 illustrated in FIG. 6, the backside (right side in FIG. 6) with respect to a direction in which the balloon catheter 110 is inserted into a blood vessel is defined as a "proximal end side" and a front side (left side in FIG. 6) with respect to a direction in which the balloon catheter 110 is inserted into a blood vessel is defined as a "distal end side".

As illustrated in FIG. 7, a guide wire tube 114, an in-side tube 117, an out-side tube 118, a cable 119, and an optical fiber 120 are inserted into and passed through the shaft 112. The outer diameter and the inner diameter of the shaft 112 do not necessarily need to be fixed with respect to the axial direction 101. However, from the viewpoint of operability, it is preferable that the rigidity of the proximal end side is higher than the rigidity of the distal end side. For the shaft 112, known materials for use in balloon catheters, such as synthetic resin and stainless steel, can be used. The shaft 112 does not necessarily need to contain only one kind of raw material and may be formed by attaching a plurality of parts containing different raw materials.

The balloon 111 provided on the distal end side of the shaft 112 is elastically expanded when a fluid (liquid, gas) flows into the internal space through the in-side tube 117 and is contracted when the liquid flows out of the internal space through the out-side tube 118. More specifically, the internal space of the balloon 111 communicates with the internal space of each of the in-side tube 117 and the out-side tube 118 inserted into and passed through the shaft 112. With respect to the size of the balloon 111, the length in the axial direction 101 is about 20 mm to 40 mm and the diameter when expanded is about 6 mm to 8 mm, for example. FIG. 6 and FIG. 7 illustrate the balloon 111 in the contracted state. For materials of the balloon 111 and a method for fixing the balloon 111 and the shaft 112, known raw materials and known methods for use in balloon catheters can be used.

On the distal end side of the shaft 112, a hub 113 is provided. The guide wire tube 114, the in-side tube 117, the out-side tube 118, the cable 119, and the optical fiber 120 are inserted into and passed through the shaft 112 through the hub 113 and are extended in the axial direction 101. More specifically, the extending directions of the guide wire tube 114, the in-side tube 117, the out-side tube 118, the cable 119, and the optical fiber 120 in the shaft 112 are substantially in agreement with the axial direction 101. The guide wire tube 114 and the in-side tube 117 are adjacent to each other inside the out-side tube 118 as illustrated in FIG. 8. The optical fiber 120 is disposed inside the in-side tube 117. Materials forming the guide wire tube 114, the in-side tube 117, and the out-side tube 118 are not particularly limited and can be formed with a thermoplastic elastomer having flexibility, such as Pebax (Registered Trademark), for example.

As illustrated in FIG. 6 and FIG. 7, the distal end of the guide wire tube 114 inserted into and passed through the inside of the shaft 112 through the hub 113 is exposed to the outside from the distal end side of the balloon 111 and is opened. The guide wire tube 114 in the balloon 111 is provided with a marker containing a contrast medium as a raw material. Examples of the contrast medium include barium sulfate, bismuth oxide, and bismuth subcarbonate, for example.

As illustrated in FIG. 7, the position of the distal end of the in-side tube 117 inserted into and passed through the inside of the shaft 112 through the hub 113 is a position P5 and the position of the distal end of the out-side tube 118 inserted into and passed through the inside of the shaft 112 through the hub 113 is a position P6. More specifically, the distal end of the in-side tube 117 is located on the distal end side of the balloon 111 relative to the distal end of the out-side tube 118. In other words, the distal end side of the in-side tube 117 is partially exposed from the out-side tube 118. However, the positional relationship between the distal ends of the in-side tube 117 and the out-side tube 118 is not particularly limited thereto.

End portions on the proximal end side of the in-side tube 117 and the out-side tube 118 are connected to a pump 131 as illustrated in FIG. 6. When the pump 131 is driven, a fluid flows into the internal space of the balloon 111 through the in-side tube 117 and a fluid flowing out of the balloon 111 returns to the pump 131 through the out-side tube 118. Then, due to the fact that a fluid continuously flows into the balloon 111 at pressure required for the balloon 111 to maintain expansion, the balloon 111 expands in the radial direction orthogonal to the axial direction 101, so that the diameter of the center in the axial direction 101 reaches the maximum diameter.

As illustrated in FIG. 7 to FIG. 9, a heat generating member 122 is provided inside the in-side tube 117 on the distal end side. In the embodiment 2, the position of the distal end of the heat generating member 122 is a position P7 and the position of the proximal end of the heat generating member 122 is a position P8. More specifically, the heat generating member 122 is provided along the inner wall surface of a portion exposed from the out-side tube 118 of the in-side tubes 117. The length in the axial direction 101 of the heat generating member 122 is about 17 mm to 35 mm and is selected as appropriate according to the length in the axial direction 101 of the balloon 111, for example.

The heat generating member 122 is a cylindrical member covering the inner wall surface of the in-side tube 117 and is obtained by winding a metal wire in a coil shape as illustrated in FIG. 9, for example. However, a specific configuration of the heat generating member 122 is not limited thereto and may be a configuration in which a metal wire is knitted in a lattice shape, a film or dot-like deposits sputtered onto the inner wall surface of the in-side tube 117, or the like, for example. Thus, the heat generating member 122 can be curved along the shape of a blood vessel into which the balloon catheter 110 is inserted. The heat generating member 122 is formed with stainless steel, for example.

The outer wall surface of the in-side tube 117 is covered with the cover tube 115. More specifically, the cover tube 115 covers a portion exposed from the out-side tube 118 of the in-side tube 117. More specifically, the cover tube 115 covers the in-side tube 117 at a position where the cover tube 115 is superimposed on the heat generating member 122 in the radial direction. More specifically, one end of the cover tube 115 is located on the distal end side of the balloon catheter 110 relative to the position P7 and the other end is located on the proximal end side of the balloon catheter 110 relative to the position P8. Materials forming the cover tube 115 are not particularly limited and polyimide can be employed, for example.

As illustrated in FIG. 7 to FIG. 9, a light-reflective metal layer 116 is laminated on the outer wall surface of the cover tube 115. More specifically, the metal layer 116 contains a first metal layer 116A contacting the outer wall surface of the cover tube 115 and a second metal layer 116B laminated on the outside of the first metal layer 116A. More specifically, the first metal layer 116A is an inner (side contacting the cover tube 115) layer and the second metal layer 116B is an outer (side exposed to the internal space of the balloon 111) layer.

The first metal layer 116A preferably contains materials having high corrosion resistance and high thermal conductivity and is formed by electroless plating using nickel or copper on the cover tube 115, for example. On the other hand, the second metal layer 116B preferably contains materials having high biocompatibility in addition to corrosion resistance and thermal conductivity and is formed by electrolytic plating using silver, gold, or platinum on the first metal layer 116A, for example. As an example, the thickness of the first metal layer 116A is about 0.1 μm and the thickness of the second metal layer 116B is about 0.4 to 0.9 μm.

As illustrated in FIG. 7, a temperature sensor 123 is provided in the internal space of the balloon 111. The installation position of the temperature sensor 123 is not particularly limited insofar as the temperature sensor 123 is installed at a position where the temperature sensor 123 contacts a fluid flowing out of the in-side tube 117. In the embodiment 2, the temperature sensor 123 is installed on the outer wall surface (more specifically, external surface of the second metal layer 116B) of the cover tube 115. A specific example of the temperature sensor 123 is not particularly limited and known substances, such as a thermocouple, can be used, for example. The cable 119 is extended in the axial direction 101 along the external surface of the second metal layer 116B and the outer wall surface of the in-side tube 117 and electrically connects the temperature sensor 123 and the control device 130. More specifically, an output signal from the temperature sensor 123 is transmitted to the control device 130 through the cable 119.

The laser generating device 125 is a known device outputting laser light beams generated under control by the control device 130. The wavelengths and the outputs of laser light beams to be generated are not particularly limited. The laser generating device 125 in the embodiment 2 can output a near-infrared laser light beam of 25 W at the maximum. The light converging optical system unit 126 has an optical element, such as a condensing lens, and connectors 127 and 128 provided at both ends of an optical path of a light beam passing through the optical element. The connector 127 is connected to the laser generating device 125 and the connector 128 is connected to the optical fiber 120. The light converging optical system unit 126 once diffuses a laser light beam input from the laser generating device 125 through the connector 127 and condense the laser light beam again, and then outputs the laser light beam to the optical fiber 120 through the connector 128.

The optical fiber 120 inserted into and passed through the inside of the shaft 112 through the hub 113 is inserted into the internal space of the in-side tube 117 in the middle of the shaft 112. Then, the optical fiber 120 is extended up to the inside of the heat generating member 122 along the shaft 112. A distal end 121 of the optical fiber 120 in the axial direction 101 is located inside the heat generating member 122 as illustrated in FIG. 7. More specifically, the distal end 121 is located on the proximal end side relative to the center of the heat generating member 122 in the axial direction 101. The optical fiber 120 is equivalent to the light guide member.

The optical fiber 120 emits a laser light beam input into the proximal end side through the light converging optical system unit 126 to the heat generating member 122 from the distal end 121. Specifically, laser light beams generated by the laser generating device 125 are input into the proximal end of the optical fiber 120 through the light converging optical system unit 126, transmitted to the distal end side while repeating total reflection in the optical fiber 120A, and then emitted to the heat generating member 122 as diffused light beams from the distal end 121.

The laser light beams output from the distal end 121 of the optical fiber 120 travel to the distal end side while repeating reflection on the inner wall surface of the heat generating member 122 as illustrated by the alternate long and short dash lines of FIG. 9. The laser light beams partially pass through a gap of the heat generating member 122 having a coil shape, transmit through the in-side tube 117 and the cover tube 115, are reflected on the metal layer 116 (more specifically, the first metal layer 116A), and then are emitted to the heat generating member 122 again as illustrated by the dashed line of FIG. 9. The laser light beams emitted to the heat generating member 122 heat the heat generating member 122. In FIG. 9, the illustration of paths after the laser light beams reflected on the metal layer 116 reach the heat generating member 122 is omitted. The diffusion angle of the laser light beams fluctuates depending on the diameter of the optical fiber 120, the frequencies of the laser light beams, and the like.

The control device 130 has an arithmetic unit controlling the entire balloon catheter device 100B. Specifically, the control device 130 measures the temperature in the balloon 111 based on an output signal obtained from the temperature sensor 123 through the cable 119. The control device 130 causes the laser generating device 125 to output laser light beams of predetermined outputs. The outputs and the irradiation time of the laser light beams are controlled based on the temperature in the balloon 111 specified by an output signal from the temperature sensor 123, for example. Furthermore, the control device 130 causes the pump 131 connected to the in-side tube 117 and the out-side tube 118 to output a fluid of a predetermined pressure and a predetermined flow rate. The fluid output from the pump 131 flows into the internal space of the balloon 111 through the in-side tube 117 and returns to the pump 31 through the out-side tube 118.

[Directions for Use of Balloon Catheter Device 100B]

Hereinafter, the directions for use of the balloon catheter device 100B are described.

The balloon catheter 110 is inserted into a blood vessel in order to expand a stenosis portion. A guide wire (not-illustrated) inserted into and passed through the blood vessel beforehand reaches the stenosis portion. The insertion of such a guide wire is performed by known techniques described in Japanese Patent Laid-Open Nos. 2006-326226 and 2006-230442, for example.

When the balloon catheter 110 is inserted into the blood vessel, a fluid is not pressed into the balloon 111, so that the balloon 111 is in a contracted state. The balloon catheter 110 in this state is inserted into a blood vessel along the guide wire inserted from the opening at the distal end of the guide wire tube 114. The insertion position of the balloon catheter 110 in the blood vessel is grasped by, for example, confirming a marker installed on the guide wire tube 114 by radiation.

After the balloon 111 reaches a desired position in the blood vessel, the pump 131 is driven under control by the control device 130, whereby a fluid flows into the in-side tube 117. The laser generating device 125 generates a laser light beam under control by the control device 130. The laser light beams emitted from the optical fiber 120 reach the heat generating member 122. A part of the laser light beams are absorbed to increase the temperature of the heat generating member 122. The other part of the laser light beams are reflected on the heat generating member 122, and travel to the distal end side of the heat generating member 122. More specifically, the laser light beams are gradually attenuated in the process of travelling to the distal end side of the heat generating member 122. The fluid flowing through the inside of the in-side tube 117 is heated by the heat generating member 122, flows into the internal space of the balloon 111, and then flows out of the balloon 111 through the out-side tube 118. The fluid flowing into the internal space of the balloon 111 expands the balloon 111 and heats the balloon 111. Thus, the pressurization due to the expansion of the balloon 111 and the heating by the generation of heat by the heat generating member 122 can be caused to act on the stenosis portion of the blood vessel.

In the heating type balloon dilation in the embodiment 2, in order to increase the temperature at a position having a depth from the cavity of the blood vessel of 0.7 mm to 55° C. (target temperature), it is necessary to increase the temperature of the balloon 111 to 70±5° C. The heating time (elapsed time after the temperature in the balloon 111 reaches a predetermined temperature) is about 17.0 seconds when the temperature in the balloon 111 is set to 65° C., is about 5.6 seconds when the temperature in the balloon 111 is set to 70° C., and is about 2.8 seconds when the temperature in the balloon 111 is set to 75° C., for example. The outputs and the irradiation time of the laser light beams are controlled by the control device 130 based on a model function showing temperature changes of the balloon 111 to the irradiation time of the laser light beam, an output signal from the temperature sensor 123, and the like.

[Operational Effects of Embodiment 2]

According to the embodiment 2, due to the employment of the heat generating member 122 in which a metal wire is wound in a coil shape, the balloon 111 can be flexibly curved along the shape of a blood vessel. Even when the laser light beams emitted from the optical fiber 120 partially pass through the heat generating member 122, the laser light beams are reflected on the metal layer 116, and thus are prevented from leaking out to the outside of the balloon catheter 110.

The light beams reflected on the metal layer 116 are emitted to the heat generating member 122 again, and therefore the heat generating member 122 can be efficiently heated. In order to increase the light quantity of the laser light beams to be reflected on the heat generating member 122 from the metal layer 116, it is preferable to form the metal layer 116 (more specifically, the first metal layer 116A) with a material having low light absorptivity. Furthermore, the metal layer 116 is also heated by the light beams passing through the heat generating member 122, and therefore, in order to promptly emit the heat to the outside, it is preferable to form the metal layer 116 with a material having high thermal conductivity.

In order to prevent overheating by the laser light beams passing through the heat generating member 122 when the outputs of the laser light beams emitted from the optical fiber 120 are high or the quantity of light beams passing through the heat generating member 122 is large, for example, the first metal layer 116A is preferably formed particularly with a material having low light absorptivity and high thermal conductivity. From this viewpoint, copper is more suitable than nickel as the material forming the first metal layer 116A. On the other hand, the adhesiveness of nickel with the cover tube 115 containing polyimide is higher than copper, and therefore when there is less concern of overheating, nickel is more suitable than copper as the material forming the first metal layer 116A.

Since the second metal layer 116B and the fluid in the balloon 111 directly contact each other, a possibility that the components of the second metal layer 116B are dissolved into the fluid cannot be ruled out. Therefore, it is preferable to form the second metal layer 116B with a material having high biocompatibility, such as silver, gold, and platinum, capable of minimizing the influence on a living body even when the fluid flows into a blood vessel due to breakage of the balloon 111. Furthermore, in order to prevent corrosion due to being exposed to physiological saline or the like which is an example of the fluid, the second metal layer 116B preferably contains the materials having high corrosion resistance as described above.

Although the embodiment 2 describes the example in which the metal layer 116 is formed on the outer wall surface of the cover tube 115, the arrangement of the metal layer 116 is not limited thereto. More specifically, the metal layer 116 may be formed on the inner wall surface of the cover tube 115 and may be formed on both the outer wall surface and the inner wall surface of the cover tube 115.

Although the embodiment 2 describes the example of the balloon catheter 110 having one optical fiber 120, the balloon catheter of the present invention is not limited thereto and may have two or more optical fibers. In this case, the number of the laser generating devices and the light converging optical systems to be disposed is the same as the number of the optical fibers. The light beams transmitted through the optical fiber 120 are not limited to laser light beams having high directivity and may be diffused light beams.

Furthermore, the embodiment 2 describes the example in which a fluid is caused to flow into the balloon 111 through the in-side tube 117 and a fluid is caused to flow out of the balloon 111 through the out-side tube 118 (i.e., fluid is caused to return). However, the present invention is not limited thereto and may be configured so that a fluid is caused to flow into the balloon 111 through the in-side tube 117 and a fluid is caused to flow out of the balloon 111 through the in-side tube 117 after the completion of the balloon dilation.

The invention claimed is:

1. A balloon catheter comprising:
a shaft having an elastically expandable balloon on a side of a distal end and space provided inside and allowing a fluid to flow into and flow out of the balloon;
a heat generating member provided in internal space of the balloon; and
a first light guide member and a second light guide member, each of which extends up to the internal space of the balloon along the shaft, and each of which emits a respective diffused light beam input into a proximal end of the heat generating member from distal ends of the respective light guide members,
wherein positions of the distal ends of the first and second light guide members are shifted from each other in an extending direction, such that the position of the distal end of the second light guide member in the extending direction is located distally in the extending direction from a position where the light beam emitted from the first light guide member reaches the heat generating member first.

2. The balloon catheter according to claim 1, wherein, the first light guide member and the second light guide member are fixed to each other.

3. The balloon catheter according to claim 1, wherein the heat generating member has a cylindrical shape.

4. The balloon catheter according to claim 1, wherein the heat generating member comprises a metal wire wound in a coil shape.

* * * * *